United States Patent
Hegyi (10) Patent No.: US 10,048,192 B2
(45) Date of Patent: Aug. 14, 2018

(54) OBTAINING SPECTRAL INFORMATION FROM MOVING OBJECTS

(71) Applicant: Palo Alto Research Center Incorporated, Palo Alto, CA (US)

(72) Inventor: Alex Hegyi, San Francisco, CA (US)

(*) Notice: Subject to any disclaimer, the term of this patent is extended or adjusted under 35 U.S.C. 154(b) by 0 days.

(21) Appl. No.: 14/576,155

(22) Filed: Dec. 18, 2014

(65) Prior Publication Data

US 2016/0178503 A1    Jun. 23, 2016

(51) Int. Cl.
*G01J 4/00* (2006.01)
*G01N 15/14* (2006.01)
*G01N 21/64* (2006.01)
*G01N 15/10* (2006.01)

(52) U.S. Cl.
CPC ..... *G01N 15/1436* (2013.01); *G01N 15/1434* (2013.01); *G01N 15/1459* (2013.01); *G01N 21/6445* (2013.01); *G01N 2015/1006* (2013.01)

(58) Field of Classification Search
CPC ............... G01J 2003/1226–2003/1252; G01J 3/45–3/4532; G01N 15/14; G01N 15/1429–15/1463
See application file for complete search history.

(56) References Cited

U.S. PATENT DOCUMENTS 3,619,061 A * 11/1971 Mitchell ............ G01N 21/6402
250/226
4,009,962 A * 3/1977 Lauer ................ G01J 3/453
356/307
4,136,954 A * 1/1979 Jamieson ............... G02B 27/58
356/456
4,320,973 A * 3/1982 Fortunato ............... G01J 3/453
356/453
4,542,295 A * 9/1985 Mattson .................. G01J 1/42
250/338.1
4,661,913 A * 4/1987 Wu ..................... G01N 15/1456
356/442
4,711,573 A 12/1987 Wjintjes et al.
(Continued)

OTHER PUBLICATIONS

Di Caprio, Giuseppe, Diane Schaak, and Ethan Schonbrun. "Hyperspectral fluorescence microfluidic (HFM) microscopy." Biomedical optics express 4.8 (2013): 1486-1493.*

(Continued)

*Primary Examiner* — Tri Ton
*Assistant Examiner* — Rufus Phillips
(74) *Attorney, Agent, or Firm* — Hollingsworth Davis, LLC (57) ABSTRACT

An optical device includes a first polarizer arranged to receive light emanating from an object moving along a trajectory. The first polarizer polarizes the light emanating from the object along a first polarization direction. A waveplate that has an optical retardance that varies as a function of position along the trajectory receives light from the first polarizer. The slow axis of the waveplate is at a first angle with respect to the first polarization direction. A second polarizer is arranged to receive light from the waveplate. The second polarizer polarizes light along a second polarization direction. At least one detector receives light from the second polarizer and provides an electrical output signal that varies with time according to intensity of the light received from the second polarizer.

19 Claims, 5 Drawing Sheets

(56) References Cited

U.S. PATENT DOCUMENTS

| | | | |
|---|---|---|---|
| 4,867,565 A | | 9/1989 | Lequime |
| 4,905,169 A | | 2/1990 | Buican et al. |
| 5,654,797 A | * | 8/1997 | Moreau ............... G01N 15/1434 356/336 |
| 5,741,640 A | * | 4/1998 | Fuller ................. C12Q 1/6806 424/94.1 |
| 5,781,293 A | | 7/1998 | Padgett et al. |
| 5,808,739 A | | 9/1998 | Turner et al. |
| 5,877,856 A | | 3/1999 | Fercher |
| 6,222,627 B1 | * | 4/2001 | Seitz ....................... G01J 3/453 356/326 |
| 6,421,131 B1 | * | 7/2002 | Miller ..................... G01J 3/447 356/453 |
| 6,473,181 B1 | | 10/2002 | Oakberg |
| 6,490,530 B1 | * | 12/2002 | Wyatt .................... G01B 1/2202 702/23 |
| 6,519,040 B1 | | 2/2003 | Amos |
| 7,106,435 B2 | | 9/2006 | Nelson |
| 7,358,476 B2 | | 4/2008 | Kiesel et al. |
| 7,440,108 B2 | | 10/2008 | Beale et al. |
| 7,471,394 B2 | | 12/2008 | Padmanabhan et al. |
| 8,233,148 B2 | | 7/2012 | Bodkin et al. |
| 8,526,002 B2 | | 9/2013 | Deflores et al. |
| 2005/0058352 A1 | | 3/2005 | Deliwala |
| 2008/0181827 A1 | | 7/2008 | Bassler et al. |
| 2008/0183418 A1 | | 7/2008 | Bassler et al. |
| 2009/0195773 A1 | | 8/2009 | Bassler et al. |
| 2009/0195852 A1 | | 8/2009 | Bassler et al. |
| 2010/0201988 A1 | | 8/2010 | Kiesel et al. |
| 2014/0226158 A1 | | 8/2014 | Trainer |
| 2014/0340520 A1 | | 11/2014 | Hay |
| 2015/0253188 A1 | | 9/2015 | Killey |

OTHER PUBLICATIONS

Ebizuka et al., "Development of a multichannel Fourier transform spectrometer", Applied Optics, vol. 34, Issue 34, 1995, pp. 7899-1906.

Harvey et al., "Birefringent Fourier-transform imaging spectrometer", Optics Express, vol. 12, No. 22, Nov. 1, 2004, pp. 5368-5374.

Kudenov et al., "Compact Snapshot Real-Time Imaging Spectrometer", Proc. of SPIE, vol. 8186, 2011, 12 pages.

Zakrzewski et al., "Advancements in Hyperspectral and Multi-Spectral Imaging", retrieved from the internet on Oct. 1, 2015, 11 pages.

Kudenov et al., "Compact snapshot birefringent imaging Fourier transformspectrometer," Optomechatronic Micro/Nano Devices and Components III: Oct. 8-10, 2007, Lausanne, Switzerland, vol. 7812, Aug. 12, 2010, p. 781206/1.

Courtial et al., "Design of a Static Fourier-Transform Spectrometer with Increased Field of View," Applied-Optics, Optical Society of America, Washington, DC, vol. 35, No. 34, Dec. 1, 1996, pp. 6698-6702.

File History for EP App. No. 15198314.5 as retrieved from the EP Electronic File System on Aug. 5, 2016, 88 pages.

File History for U.S. Appl. No. 14/944,446, 132 pages.

File History for U.S. Appl. No. 14/944,446, 234 pages.

\* cited by examiner

OBTAINING SPECTRAL INFORMATION FROM MOVING OBJECTS

TECHNICAL FIELD

This disclosure relates generally to devices, systems and methods for determining characteristics of moving objects.

BACKGROUND

Various techniques have been proposed for performing sample analysis using light emanating from objects. For example, U.S. Pat. No. 7,358,476 (Kiesel et al.) discusses a fluidic structure with a channel along which is a series of sensing components to obtain information about objects traveling within the channel, such as droplets or other objects carried by a fluid. A sensing component includes a set of cells that photosense a range of photon energies that emanate from objects. A processor receives information about objects from the sensing components and uses it to obtain spectral information. Additional techniques are described, for example, in U.S. Patent Application Publications 2008/0181827 (Bassler et al.), 2008/0183418 (Bassler et al.), 2009/0195773 (Bassler et al.), 2009/0195852 (Bassler et al.), and 2010/0201988 (Kiesel et al.).

Also, various flow cytometry techniques have been proposed.

SUMMARY

Some embodiments described herein are directed to an optical device that includes a first polarizer arranged to receive light emanating from an object moving along a trajectory of a flow path. The first polarizer polarizes the light emanating from the object along a first polarization direction. A waveplate is arranged to receive light from the first polarizer, the waveplate having an optical retardance that varies as a function of position along the trajectory direction and having a slow axis at a first angle, e.g., about 45 degrees, to the first polarization direction. A second polarizer is arranged to receive light from the waveplate. The second polarizer polarizes light received from the waveplate along a second polarization direction that may be about parallel or about perpendicular with respect to the first polarization direction. At least one detector is optically coupled to receive light from the second polarizer. The detector provides an electrical output signal that varies with time according to intensity of the light received from the second polarizer.

The light emanating from the object may be scattered light, reflected light, fluorescence light, phosphorescence light, chemiluminescence light, or bioluminescence light, for example. The optical device may further include a lens configured to image the light emanating from the object on the waveplate. Optionally the first polarizer and/or the second polarizer is a polarizing beamsplitter. In some configurations, the waveplate is a Wollaston prism.

Optionally, the optical detector may include a spatial mask, wherein a portion of the light emanating from the object, e.g., about half, is spatially modulated by the spatial mask and the detector is arranged to receive the spatially modulated light. Optionally, the optical detector may include one or more optical bandpass filters configured to limit a bandwidth of the light received by the detector.

Some embodiments are directed to a system that includes an optical device as discussed above and a processor configured to process the detector output signal and to determine information about the objects. The processor may determine the optical spectra of one or more of the objects based on the detector output signal. The processor may determine object type based on the optical spectra of the objects and/or may determine other object characteristics.

The processor may use the spatially modulated light to determine velocities of the one or more objects. In some implementations the portion of the detector output signal responsive to the spatially modulated light may include a first frequency component that is different from and/or orthogonal to a second frequency component of the detector output signal that is responsive to light received from the second polarizer.

In some implementations the optical device includes one or more optical bandpass filters configured to limit a bandwidth of the light received by the detector. The processor may apply various correction factors that correct for properties of the optical components. For example, the processor may correct for optical dispersion in the waveplate and/or the processor may correct for angle of incidence of the emanating light.

According to some aspects, multiple detectors are used wherein each detector generates a detector output signal. The first detector output signal may be responsive to a light polarized along one direction and the second detector output signal may be responsive to light polarized along another direction. The processor combines the output signals of the multiple detectors and processes the combined output signal to determine information about the one or more objects.

According to some configurations, the optical device and processor are components of a flow cytometer. In these configurations the processor may be configured to determine presence and/or amount of one or more of objects and/or analytes based on the detector output signal. The processor can include multiple electronic (hardware or software) filters, each electronic filter associated with an optical channel of the flow cytometer. According to some implementations, the electronic filters can be modified either manually or automatically during operation.

Some embodiments are directed to a method. Light emanating from an object moving along a trajectory is polarized along a first polarization direction. After the light is polarized along the first polarization direction, a waveplate having a retardance that varies as a function of position along the trajectory direction is used to create a varying polarization of the light. The varying polarization of the light is converted to a varying intensity of the light and is detected and a time varying electrical signal is generated in response to the detected light.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Embodiments described herein involve devices, systems, and methods for determining characteristics of moving objects. Many embodiments are particularly applicable to the field of flow cytometry. Approaches involve obtaining a high resolution optical spectrum from a moving object emanating light, in some cases, using one single pixel detector. The optical spectrum is obtained at high resolution, without decreasing the optical throughput or the spectral bandwidth, by using the object motion to generate an interferogram. In the embodiments described below, the optical device, which may be referred to herein as a "spectrum encoder," converts the optical signal from light emanating one or more moving objects to an electrical signal, wherein the electrical signal encodes spectral information from each of the objects in the frequency domain of the electrical signal. The electrical signal can be processed by electrical circuitry, referred to herein as a processor, to extract the spectral information. Extraction of the information can involve transformation of the electrical signal from time domain to frequency domain such as by performing a full Fourier transform of the electrical signal or a partial Fourier transform of the electrical signal at one or more predetermined frequencies of interest.

Figure 1:
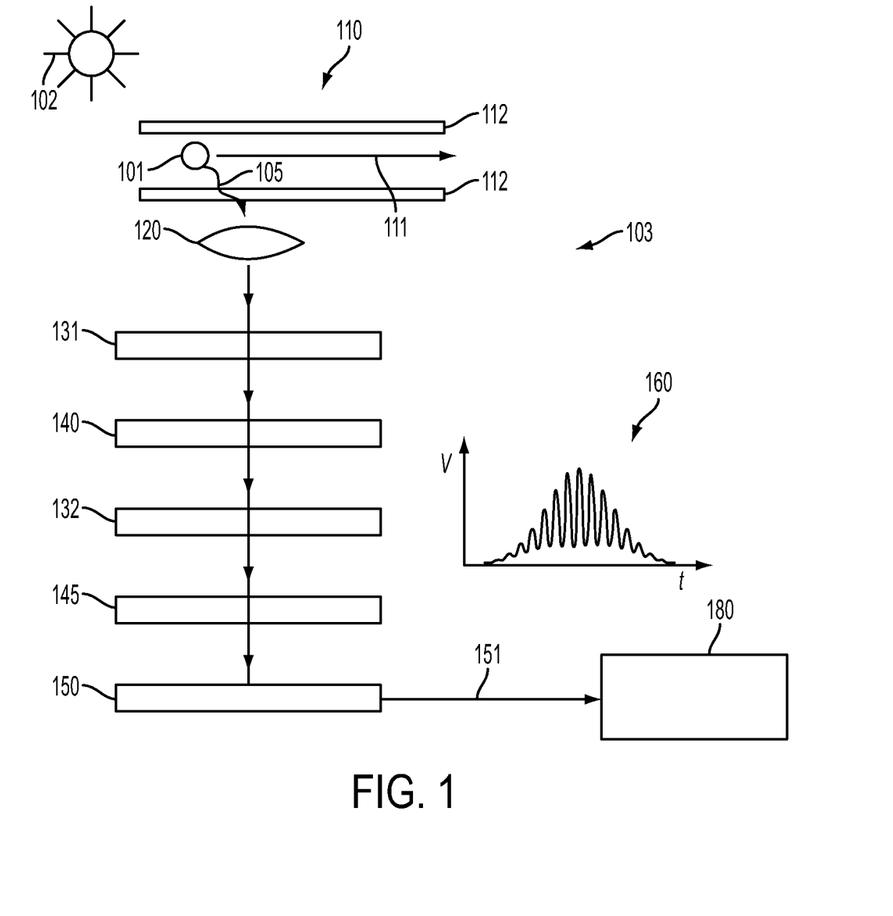
FIG. 1 is a block diagram of a system in accordance with some embodiments.

FIG. 1 illustrates a system comprising an optical device 103 configured to provide an electrical signal that includes information about characteristics of a moving object. FIG. 1 shows one or more moving objects 101 moving in a trajectory 111 along a flow path 110. In some implementations, the flow path may be disposed between channel walls 112 that constrain the object movement to trajectory 111. Although not shown in FIG. 1, in some embodiments, a fluid movement device, e.g., comprising one or more pumps and/or one or more valves, may be coupled to the flow channel between the channel walls 112, wherein the fluid movement device is configured to cause the movement of the object 101 along the trajectory 111. Light 105 emanates from each of the objects 101. Optionally, the optical device 103 may include a light source 102 configured to provide input light that interacts with the objects 101. In response to the input light, the objects emanate light. For example, the emanating light 105 may be or comprise scattered light, reflected light, fluorescence light, phosphorescence light, chemiluminescence light, bioluminescence light, etc.

In embodiments that include flow channel walls, at least one of the walls may be optically transparent to the input light and at least one of the walls may be optically transparent to the emanating light 105. The optical device 103 includes one or more first polarizers, represented in this example by first polarizer 131. The first polarizer 131 is configured to receive the light 105 emanating from the object 101. Optionally, a lens 120 may be arranged between the object and the first polarizer 131 such that the lens 120 focuses the emanating light 105, e.g., halfway between the surfaces of the waveplate 140. Alternatively, the trajectory 111 of the object may bring the object 101 sufficiently close to the waveplate 140 so that a lens is not needed. In embodiments that include a lens, the lens can be configured to be chromatically correct so that all frequencies of light are substantially focused halfway between the surfaces of the waveplate 140.

The emanating light 105 passes through the first polarizer 131 which polarizes the light along a first polarization direction. Light that has been polarized along the first polarization direction is received by a waveplate 140, e.g. a multiple (high) order waveplate, sandwiched between the first polarizer 131 and a second polarizer 132. The waveplate 140 has an optical retardance that varies as a function of position along the trajectory direction 111 of the object 101. In some configurations, the retardance varies monotonically or linearly as a function of position along the trajectory direction 111 of the object 101. In some configurations, the waveplate may be a Wollaston prism or other optical retardance device, positioned such that there is about zero optical retardance between the two polarizations of light after propagation through the waveplate when the object is roughly at the center of the field of view of the detector. This ensures that the recorded interferogram is substantially centered about its zeroth order fringe.

The second polarizer 132 shown in FIG. 1 represents one or more second polarizers. The polarization axes of the first and second polarizers 131, 132 may be arranged in either a parallel or perpendicular orientation. In some implementations, the first and second polarizers 131, 132 are crossed polarizers, the first polarizer 131 having a polarization axis that is about 90 degrees from the polarization axis of the second polarizer 132. The slow axis of the waveplate 140 makes a first angle, e.g., about 45 degrees, with respect to the polarization axes of the first and second polarizers 131, 132.

The object's movement relative to the position-dependent phase delay of the waveplate 140 creates a time-dependent variation in polarization of the emanating light that is dependent on the optical spectrum of the light. The varying polarization of light is converted to a varying intensity by the second polarizer 132. A detector 150, e.g., a single pixel detector, converts the time varying intensity of light to a time varying electrical output signal, e.g., time varying voltage, at the output 151 of the detector. For narrow band light, the time variation in the light intensity may be oscillatory, with oscillation period dependent on the center wavelength of the band. Graph 160 illustrates an example of the time varying output signal of the detector associated with one object moving along the trajectory 111 while emanating light in a narrow band of wavelengths. The output signal includes information about the object 101, such as the spectrum of the light emanating from the object.

Optionally, the optical device 103 includes one or more optical filters 145. For example, in various embodiments, an optical filter may be arranged anywhere in the light path between the object 101 and the detector 150, e.g., between the second polarizer 132 and the detector 150 as shown in FIG. 1. The optical filter 145 can serve to limit the bandwidth of the light incident on the detector 150 to a bandwidth range of interest which simplifies signal processing. In some cases, limiting the bandwidth of the light received by the detector allows full recovery of the spectral information from the optical interferogram generated by the motion of the object, even if the electrical signal generated by the interferogram is sampled below the Nyquist limit (two samples per interference fringe).

The system shown in FIG. 1 includes a processor 180 coupled to receive the electrical output signal from the detector 150. The processor 180 includes circuitry, such as a processor that executes programmed instructions, configured to process the output signal to extract information about the object 101. Note that the size of the object may be small with respect to the field of view of the detector 150, so that the light interference fringes created by the motion of the object 101 and detected by the detector 150 can be resolved by the processor 180. For example, if N interference fringes are to be recorded as the object traverses the field of view of the detector, the size of the object 101 along the trajectory direction 111 may be about 1/2N of the field of view of the detector 150 along the trajectory direction 111, or smaller, to resolve the interference fringes.

Figure 2:
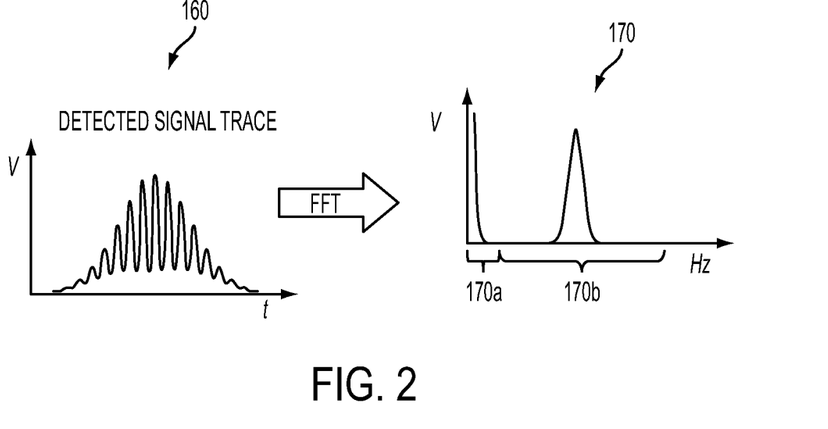
FIG. 2 illustrates conversion of the detector output to a frequency domain signal in accordance with some embodiments.

The output of the detector can be processed, e.g., such as by Fourier transformation or other time to frequency domain transformation, to determine the optical spectrum of the light emanating from the object. As shown in FIG. 2, the transformed output signal 170 may include lower frequency components 170a and higher frequency components 170b. The lower frequency components 170a are associated with the envelope of the signal 160 and the higher frequency components 170b correspond to the optical spectrum of the emanating light.

In one example, the waveplate is a Wollaston prism having a wedge angle α, where wedge angle is defined as the angle between the front face of the prism which is normal to the optical axis, and the interior face where the two halves of the prism are cemented together. The slow axes of the prism may be oriented at about 45 degrees with respect to the axes of the polarizers. The wedge direction of the prism is defined as the direction, in a plane parallel to the front face of the prism, along which the thicknesses of the two halves of the prism trade off the fastest. It is preferable to align the prism's wedge direction with the object's trajectory. If the desired spectral resolution at wavelength λ is λ/N, N fringes must be recorded as the object traverses across the field of view. If the travel distance of the object or the image of the object is L along the wedge direction of the Wollaston prism with birefringence Δn, the wedge angle of the Wollaston should be α≈Nλ/2LΔn. The maximum spectral bandwidth is limited by the sample rate of the detector signal, which must be fast enough to record the observed fringes. The spectral bandwidth is also limited by the size of the object. If the object diameter is d, then the maximum number of fringes that can be recorded by the detector is approximately L/2d, so the minimum detectable wavelength is λ≈4αdΔn.

According to the approaches discussed herein, the object's motion is used to encode spectral information in the time varying signal of at least one single-pixel detector such that the object's spectral information is encoded in the frequency domain of the time varying signal. Using these approaches, it is possible to use one single-pixel detector with a single output to obtain the emanating light spectrum, and there is no significant loss of optical throughput with increasing spectral resolution as occurs with conventional spectroscopy. In some implementations, the outputs of two or more single pixel detectors are combined to enhance signal to noise ratio of the combined signal.

Figure 3:
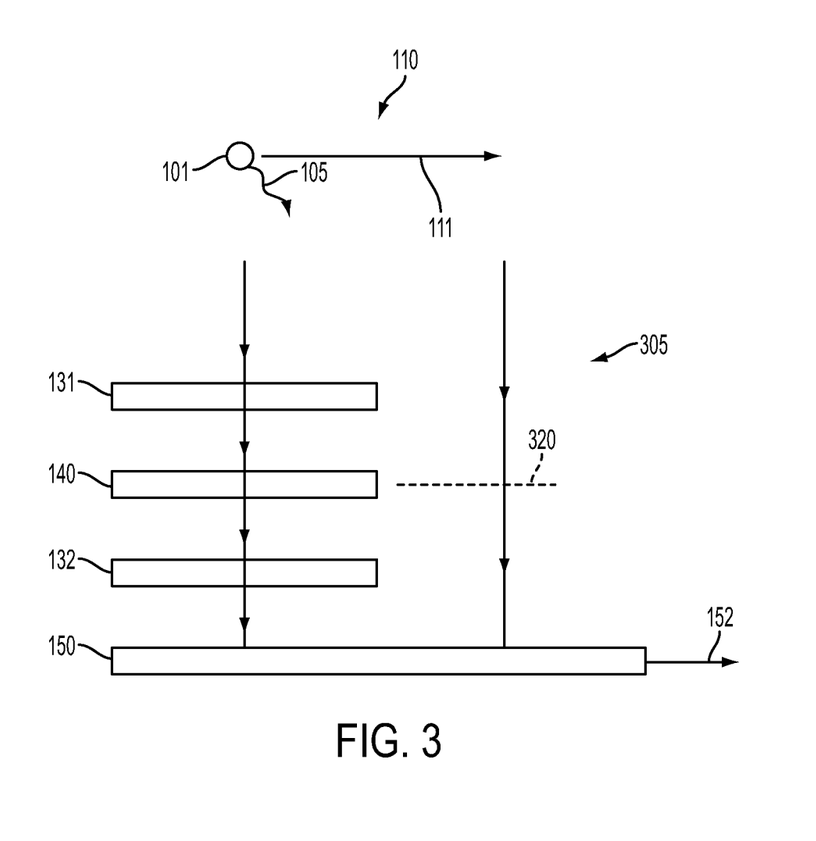
FIG. 3 shows an optical device that includes a spatial filter in accordance with some embodiments.

FIG. 3 shows optical device 305 that is similar in some respects to the optical device 103 of FIG. 1. Optical device 305 includes a waveplate 140 sandwiched between first and second polarizers 131, 132. The emanating light 105 from moving object 101 traveling along trajectory 111 passes through the first polarizer 131 which polarizes the light along a first polarization direction. The light polarized by the first polarizer is received by a waveplate 140 that has an optical retardance that varies as a function of position along the trajectory direction 111.

At each wavelength, the phase delay in the emanating light caused by the waveplate 140 creates a varying polarization that is dependent on the wavelength. The varying polarization of light is converted to a varying light intensity by the second polarizer 132. The light from the second polarizer falls on detector 150. In some configurations, the light is filtered by optional optical filter 145 which is arranged in the light path between the second polarizer 132 and the detector 150.

Optical device 305 additionally includes a spatial mask 320 that includes a number, e.g., 3, 4, 5, or more, mask features that are optically transparent to the emanating light alternating with 3, 4, 5, or more optically opaque mask features. A portion of the light 105 emanating from the object may be imaged on the spatial mask 320. The spatial mask 320 interacts with the light emanating 105 from object 101 and the interaction creates a time varying light that is incident on the detector 150. It will be appreciated that the movement of object 101 along the trajectory provides a time multiplexed signal at the output 152 of the detector 150. The time multiplexed signal at the output 152 of the detector 150 includes a first time multiplexed portion that corresponds to the varying light intensity from the second polarizer 132 and a second time multiplexed portion that corresponds to the time varying light caused by the interaction between the emanating light 105 and the spatial mask 320. It will be appreciated that the optical device 305 may optionally be arranged so that the first portion of the output signal 152 corresponds to the time varying light from the spatial mask 320 and the second portion corresponds to the varying intensity at the output of the second polarizer 132. The first time portion of the signal responsive to the varying intensity light from the second polarizer may be processed to extract first information about the object, e.g., the optical spectrum of the light emanating from the object. The second portion of the signal responsive to the time varying light caused by interaction of the emanating light with the spatial mask may be processed to extract second information about the object, such as velocity and/or size of the object. The second information may be used to apply a correction to the first information, such as using object velocity information to calibrate the wavelength scale of the optical spectrum.

According to some implementations, the output signal can be analyzed without time demultiplexing the signal 152 into the first and second portions. This scenario may occur when the optical bandwidth of the light 105 emanating from the object 101 is known not to exceed a certain range so that the fringes of the interferogram detected at the detector should also lie within a certain bandwidth. If this is the case, then a portion of the emanating light can be imaged onto the spatial mask which may be placed adjacent to the waveplate as shown, e.g., half the emanating light falling on the spatial mask, while simultaneously half of the emanating light falls on the first polarizer as shown. The intensity variations caused by the spatial mask lie outside of the frequency range of the interferogram fringes generated by the polarizer/waveplate/polarizer structure. Thus, light falling on the polarizer/waveplate/polarizer structure and light falling on the spatial mask can be combined onto the same detector 150. The electrical output signal component responsive to the polarizer/waveplate/polarizer structure and the signal component responsive to light modulated by the spatial mask in the output signal 152 can be separated in software. This separation is possible because the light from the polarizer/waveplate/polarizer structure lies in a frequency range that is substantially orthogonal to the spatially modulated light from the spatial mask.

Figure 4:
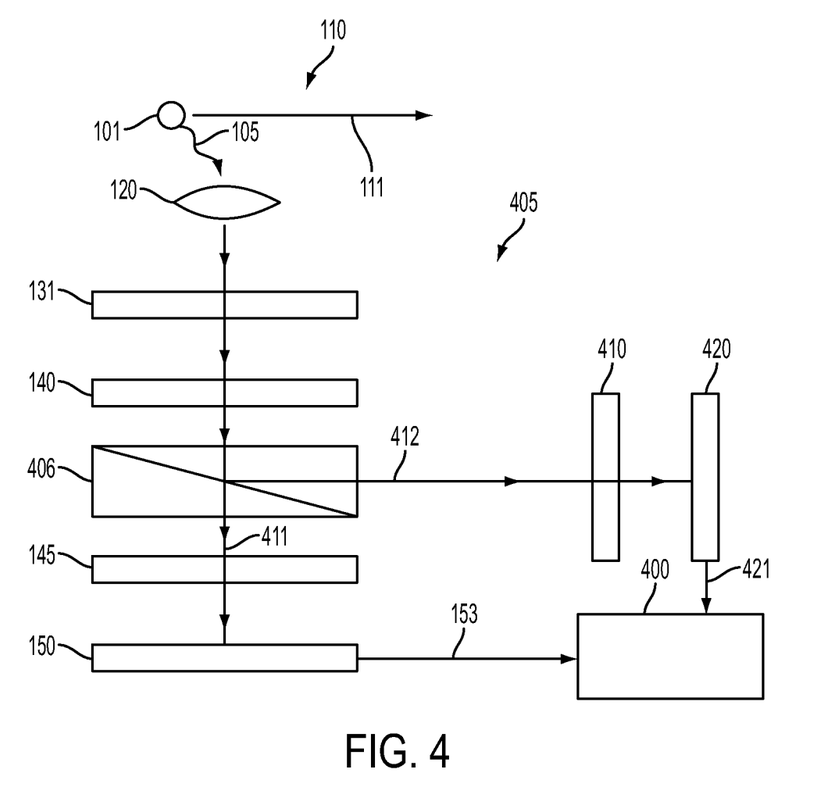
FIG. 4 depicts an optical device that includes a polarizing beamsplitter and multiple detectors in accordance with some embodiments.

In some embodiments, each of the first and second polarizers can optionally be replaced by a polarizing beamsplitter. In some embodiments, two (or more) single pixel detectors can be used to detect light having different polarizations. FIG. 4 illustrates an optical device 405 that includes a polarizing beamsplitter 406 in the place of the second polarizer shown in FIG. 3. The first polarizer 131 polarizes the light emanating 105 from the object 101 along a first polarization direction. The polarizing beamsplitter 406 splits the light from the waveplate 140 into light 411 polarized along a second polarization direction and light 412 polarized along a third polarization direction. For example, one of the polarization axes of the polarizing beamsplitter 406 could be chosen to lie at 45 degrees with respect to a slow axis of the waveplate 140 as viewed along the optical axis. Detector 150 is arranged to detect light 411 polarized along the second direction. Detector 420 is arranged to detect light 412 polarized along the third polarization direction. Optional components 145, 410 may be respectively disposed in the light path between the polarizing beam splitter 406 and detector 150 and/or in the light path between polarizing beam splitter 406 and detector 420. In some embodiments, the optional components 145, 410 comprise optical filters that optically filter light 411 and 412. In some embodiments, component 145 and/or component 410 may be or comprise a spatial mask. Components 145, 410 can additionally include optics that image the emanating light from the object onto the spatial filters. The outputs 153, 421 of the detectors 150, 420 are both coupled to processor 400. The processor 400 may be configured to analyze outputs to enhance optical throughput and signal to noise ratio of the optical device.

In embodiments in which components 145 and/or 410 comprise spatial masks, the processor 400 can extract additional information about the objects, such as object speed and/or size, based on time variation in the electrical signal caused by the spatial mask. Interaction of the emanating light with a spatial mask generates frequency components in the electrical output signal 153, 421 of a detector 150, 420 that can be discriminated from the frequency components that result from varying light intensity caused by a time dependent variation in polarization.

Figure 5:
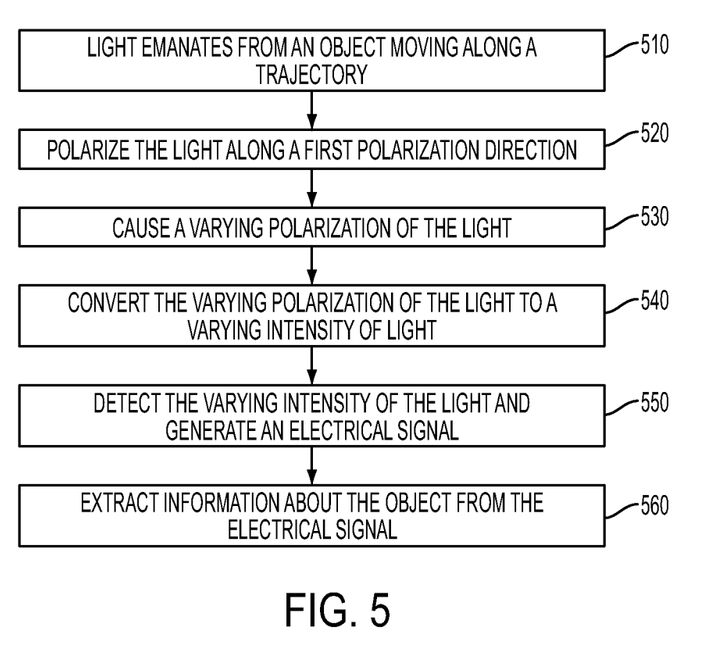
FIG. 5 is a flow diagram illustrating a method according to a some embodiments.

FIG. 5 is a flow diagram of a method of operating the optical detector and processor discussed herein. Light emanates 510 from one or more objects moving along a trajectory. The emanating light is polarized 520 along a first polarization direction. A varying polarization of the light is created 530 by a waveplate having a variable retardance along the trajectory of the object. The varying polarization is transformed 540 into a time varying intensity of light. A time varying electrical signal is generated 550 in response to the time varying intensity of light. The time varying electrical signal includes information about one or more characteristics of the object. For example, the information may be encoded in the fluorescence spectrum of light emanating from the object. The time varying electrical signal is analyzed 560 to extract information about the spectrum of the light emanating from the object.

In some implementations, such as flow cytometry, it is useful to have the capability of detecting light in individual channels across a relatively wide optical bandwidth range. Traditionally this has been accomplished using filter wheels to define the individual fluorescence channels that are fixed by the hardware. Another technique has used a prism to disperse light and a photomultiplier tube array to detect the dispersed light. Still other techniques rely on the use of spatial modulation of the emanating light that is resolved into channels by a linear variable filter. Drawbacks to these techniques include inflexibility due to hardware limitations, expensive detector arrays, and/or loss of spectral resolution and/or optical throughput. Approaches described herein can be employed to mitigate these factors.

Approaches described herein provide for detecting the spectra at high spectral resolution of light emanating from one or more moving objects. These approaches use a single pixel detector and are absent of tradeoffs between optical throughput and spectral resolution that affect conventional forms of spectroscopy. These approaches involve using the object's motion to generate an interferogram and to convert the interferogram to an electrical signal using a single pixel detector. In some implementations only one single pixel detector is used and in some cases multiple single pixel detectors are used. Spectral information of the emanating light is encoded in the frequency domain of the electrical signal. The spectral information can be extracted from the output signal of the detector using a time domain to frequency domain transformation such as a Fourier transform. As in other forms of Fourier spectroscopy, light at all wavelengths is recorded simultaneously, so there is no tradeoff between spectral resolution and optical throughput.

In various embodiments, the optical device and/or processor shown and described, for example, in FIGS. 1-5 may be implemented in a flow cytometer that can be configured to analyze objects and/or analytes that are bound to the objects present in a sample. In these embodiments, the processor may have the capability of processing the electrical signal using one or multiple processing channels wherein each processing channel corresponds to a particular fluorescence channel of the flow cytometer. The processing channels may be electrical hardware channels and/or may be reconfigurable software channels. For example, in some implementations, the emanating light from objects moving in the flow channel of the flow cytometer is detected, transformed to an electrical signal, sampled, and stored. Information may be extracted from each processing channel by passing the electrical signal through one or more analog and/or digital electronic filters. For example, each processing channel may correspond to a spectral slice (frequency range) of the electrical signal. In some implementations, the processor can be programmed to automatically determine the processing channels to be used, e.g., the number and/or frequency ranges of channels that are optimal for the optical signal, based on the expected and/or observed spectral components of the electrical signal. In some embodiments, the processor may determine optimal filter coefficients and/or configurations for the channel filters. The channel filters can be modified before and/or during operation of the flow cytometer, e.g., either manually or automatically.

In some embodiments, the processor can be configured to determine an optimal number of processing channels and/or optimal frequency ranges of the processing channels using a clustering algorithm. According to some implementations, to determine the optimal channels, the processor analyzes the electrical signal and identifies groups of different object populations that are clustered based on spectral information. These clustered groups are then used to determine the optimal number and/or frequency ranges of the processor channels. In some implementations, the electronic filters can be modified either manually or automatically during operation.

As previously discussed, in some implementations, more than one single pixel detector may be used wherein each detector detects a different polarization of the emanating light. The electrical signals from each of the detectors and/or time domain to frequency domain transformations of these signals may be stored, combined, and/or used to analyze the spectra of light emanating from the one or more objects. For example, if optical signals of opposite polarizations were detected by the same detector, the oppositely polarized optical signals would tend to cancel each other out because the interferogram measured at one polarization has the opposite phase as the interferogram measured at an orthogonal polarization. Using two detectors, the signals from each of the detectors can be processed before combining so that the signals are in phase and thus additive rather than subtractive. For example, the time varying signal from one of the detectors may be phase inverted, or the signals from both detectors may be transformed from the time domain to the frequency domain, prior to combining. The combination of the two signals can increase the optical throughput of the optical device relative to a single signal and, correspondingly, the signal to noise ratio of the combined signal is increased. In some scenarios, a polarizing beamsplitter is used in place of each of the first and second polarizers. In these scenarios, it is necessary to place two waveplates or Wollaston prisms after the first polarizing beamsplitter, so there is one waveplate for each polarization exiting the first polarizing beamsplitter. Each waveplate or Wollaston should be oriented so that a slow axis is about 45 degrees with respect to a polarization axis of the beamsplitter when viewed from the waveplate or Wollaston's optical axis. The wedge axis of the waveplate or Wollaston, i.e., the direction transverse to the waveplate or Wollaston's thickness direction along which the optical retardance varies, should be about parallel with the object trajectory. A polarizing beamsplitter and a pair of detectors is then placed after each waveplate, with a polarization direction parallel to one of the polarization directions of the first polarizing beamsplitter. Thus, in total, there are three polarizing beamsplitters and four detectors, each detector arranged to detect one of the two light polarized light beams produced by the second or third polarizing beamsplitters. By detecting all polarization combinations of light, this configuration with four detectors has up to four times the optical throughput as the single-pixel detector configuration.

In some embodiments, the processor may first detect and trigger on the presence of an object in the flow path based on characteristics of the electrical signal, such as whether the electrical signal's amplitude lies above a threshold value. The triggered portion of the signal, perhaps including pre-trigger and posttrigger samples, may be selected for further processing, such as transformation to the frequency domain. The spectral information associated with each detected object is encoded in the frequency components of the electrical signal. When the frequency components associated with the optical spectra of light emanating from different types of objects differ, the processor can discriminate objects of different types based on transformations of the electrical signal.

In some embodiments, the analysis may only include transformation of certain frequency ranges or portions of the electrical signal, rather than a full transformation across a wide frequency range. In these embodiments, optical filters may be placed before the detectors, or the processor may use software and/or hardware digital and/or analog filters, to remove or reduce frequency components in the signal that are not of interest prior to performing the time domain to frequency domain transformation. Or, the processor may use software and/or hardware digital and/or analog filters as a means to directly pick out frequency components of interest in the electrical signal, in some cases obviating further transformation.

Approaches described herein allow flexibility in processing the entire frequency range of the electrical signal or processing only specified portions of the frequency range (frequency slices) of the electrical signal that correspond to colors (optical spectrum ranges) of interest without the need to process other frequency ranges that are not of interest. In some embodiments, the processing makes use of adaptable filters having parameters that can be automatically adjusted by the processor and/or can be semi-automatically adjusted based on some input from the user. For example, in one scenario, the processor may determine which frequency components are present in the electrical signal and determine the number and frequency ranges of the filters used. In another scenario, a user may input information related to expected frequency ranges of the electrical signal (or frequency ranges of interest) and the processor may initially use those frequency ranges to set up the filters and may automatically make adjustments.

The processor may determine the frequency range(s) in the electrical signal corresponding to optical spectra of interest using a clustering algorithm to group frequencies or frequency ranges of object populations and to determine the highest fidelity separation between object types present in a sample based on variation of these frequency ranges. In some embodiments the clustering algorithm may be or comprise a principal component analysis of the electrical signal. For example, consider the scenario wherein the clustering algorithm identifies M different object types corresponding to M optical spectra and M principal components of the electrical signal. The processor can then detect the object types having any of those M optical spectra of interest by performing a dot product of each of the M principal components with the electrical signal in the time domain. The results of the dot product comprise a vector in a subdivided M-dimensional space, whereby the presence of the vector in one region of that space may indicate that an object of a particular type has been detected. Fourier transformation of the electrical signal may not be necessary when utilizing this technique.

In some embodiments, the processor is capable of correcting for errors caused by physical properties of the waveplate and/or other optical components of the optical device. For example, consider that the number of fringes is dependent on wavelength and on birefringence $\Delta n$. However, birefringence is also dependent on wavelength, thus a correction factor is needed to accurately relate the frequency of the electrical signal to the optical spectrum of the object. Otherwise, calibration at one frequency of the electrical signal (Fourier component) would not be applicable across other frequencies/Fourier components. This correction factor may be determined and applied for in the processor, for example using the known wavelength dependence of the birefringence.

In general, light from the object incident on the waveplate will be substantially collimated. However, software correction may also be needed to account for the difference in optical retardance as a function of angle of the light incident on the waveplate. The changing angle is caused by a change in position of the moving object as it or its image moves laterally across the waveplate surface.

In various embodiments, all or part of the optical device and/or processor may be implemented in opto-electronic hardware. In some exemplary embodiments, functions of the processor may be implemented in firmware, software running on a microcontroller or other device, or any combination of hardware, software and firmware.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. A method, comprising:
receiving emanating light from an object or image of the object (object/object image) moving along a trajectory relative to a waveplate of a spectral encoder, the object/object image traversing a distance, L, along the trajectory within a field of view of the spectral encoder, the object/object image having a diameter, d, along the trajectory;
obtaining spectral information for the object/image point by generating a position-dependent polarization interferogram from the emanating light including generating N interference fringes based on motion of the object/object image, the N interference fringes generated from light at wavelength $\lambda$ emanating from the object/object image as the object/object image moves the distance L along the the trajectory, wherein L≥2dN, wherein generating the N interference fringes comprises:
polarizing light along a first polarization direction, the light emanating from the object/object image moving along the trajectory;
after polarizing the light along the first direction, causing a time dependent variation in polarization of the light that is dependent on an optical spectrum of the light and movement of the object/object image along the trajectory, the time dependent variation in polarization of the light provided by a waveplate having an optical retardance that varies as a function of position along the trajectory and having a slow axis at an angle to the first polarization direction; and
converting the time dependent variation in polarization of the light to a time varying intensity of the light by polarizing the light received from the waveplate along a second polarization direction; and
wherein obtaining spectral information comprises detecting the time varying intensity of the light and generating a time varying electrical signal in response to the time varying intensity of the light, the time varying electrical output signal encoding spectral information about the object/object image with spectral resolution at wavelength $\lambda$ of about $\lambda/N$.

2. The method of claim 1, further comprising analyzing the time varying electrical signal using an algorithm to determine a number of processing channels and/or frequency ranges of the processing channels based on a transformation of the electrical signal.

3. The method of claim 1, further comprising imaging the light emanating from the object/object image on the waveplate.

4. The method of claim 1, further comprising spatially modulating a portion of the light emanating from the object/object image.

5. The method of claim 4, further comprising determining a velocity of the object based on the portion of the light emanating from the object/object image that is spatially modulated.

6. The method of claim 1, further comprising:
processing the time varying electrical signal; and
determining information about the object based on the time varying electrical signal.

7. The method of claim 1, further comprising determining an optical spectrum of the light emanating from the object/object image based on the time varying electrical signal.

8. The method of claim 1, further comprising identifying an object type based on the time varying electrical signal.

9. The method of claim 1, wherein:
generating the time varying electrical signal comprises generating multiple time varying electrical signals in response to a specified polarization of light; and
combining the time varying output signals to form a combined output signal;
processing the combined output signal to determine information about the object/object image.

10. A system, comprising:
a spectral encoder configured to receive emanating light from an object or image of an object (object/object image) as the object/object image moves along a trajectory relative to a waveplate of the spectral encoder, the spectral encoder comprising:
a first polarizer configured to polarize light received by the spectral encoder along a first polarization direction;
the waveplate which is configured to cause a time dependent variation in polarization of the light that is dependent on an optical spectrum of the light and movement of the object/object image along the trajectory, the waveplate having an optical retardance that varies as a function of position along the trajectory and having a slow axis at an angle to the first polarization direction;
a second polarizer configured to convert the time dependent variation in polarization of the light to a time varying intensity of the light by polarizing the light received from the waveplate along a second polarization direction,
wherein the spectral encoder generates a position-dependent polarization interferogram that includes N interference fringes based on motion of the object/object image, the N interference fringes generated from light at wavelength $\lambda$ emanating from the object/object image as the object/object image traverses the distance L within a field of view of the spectral encoder, wherein the object/object image has a diameter, d, along the trajectory and L≥2dN; and
circuitry configured to:
obtain spectral information for the object/object image from the spectral encoder; and
generate a time varying electrical output signal in response to the time varying intensity of the light, the time varying electrical output signal encoding spectral information about the object/object image with spectral resolution at wavelength $\lambda$ of about $\lambda/N$.

11. The system of claim 10, wherein:
the optical device and processor are components of a flow cytometer; and
further comprising a processor configured to determine presence and/or amount of one or more of objects and analytes based on the time varying electrical output signal.

12. The system of claim 11, wherein the processor comprises multiple digital filters, each digital filter associated with a channel of the flow cytometer.

13. The system of claim 10, wherein:
the circuitry comprises multiple detectors, each detector generating a time varying electrical output signal in response to a specified polarization of light; and the circuitry further comprises a processor configured to combine the time varying electrical output signals of the multiple detectors and to process the combined output signal.

14. The system of claim 10, further comprising a spatial mask, wherein a portion of the light emanating from the object/object image is spatially modulated by the spatial mask and the circuitry is arranged to receive the spatially modulated light.

15. The system of claim 10, wherein the circuitry further comprises a processor configured to determine an optical spectrum of the light emanating from the object/object image based on the time varying electrical output signal.

16. The system of claim 10, wherein the circuitry further comprises a processor configured to identify an object type of the object/object image based on the time varying electrical output signal.

17. The system of claim 10, wherein the circuitry further comprises a processor configured to determine velocity of the object based on the portion of the detector output signal responsive to the spatially modulated light.

18. The system of claim 10, wherein the circuitry comprises a processor configured to transform the time varying electrical output signal from a time domain signal to a frequency domain signal and to extract information about the object/object image from the frequency domain signal.

19. The system of claim 10, wherein the circuitry includes a processor configured to process the time varying electrical output signal to correct for optical properties of one or more components of the spectral encoder.

* * * * *